United States Patent [19]
Fuxe

[11] 3,991,198
[45] Nov. 9, 1976

[54] METHOD OF TREATING DEPRESSION

[75] Inventor: Kjell Fuxe, Sollentuna, Sweden

[73] Assignee: Nelson Research & Development Company, Irvine, Calif.

[22] Filed: June 25, 1975

[21] Appl. No.: 590,193

Related U.S. Application Data

[62] Division of Ser. No. 475,858, June 3, 1974, Pat. No. 3,904,758.

[52] U.S. Cl. ............................................. 424/267
[51] Int. Cl.$^2$ .................................... A61K 31/445
[58] Field of Search ................... 424/267, 247, 319

[56]   References Cited
       UNITED STATES PATENTS
2,056,046   9/1936   Fourneau ...................... 260/293.58

Primary Examiner—Stanley J. Friedman
Attorney, Agent, or Firm—Martin A. Voet

[57] ABSTRACT

Methods of temporarily alleviating symptoms of hypersomnia or mental fatigue or drowsiness or temporarily suppressing appetite by administering to a human or animal having one or more of the aforementioned symptoms an effective amount of piperoxan together with a suitable pharmaceutical carrier. Piperoxan is also useful for potentiating the effects of antidepressant drugs.

1 Claim, No Drawings

METHOD OF TREATING DEPRESSION

This is a division of application Ser. No. 475,858, filed June 3, 1974, now U.S. Pat. No. 3,904,758.

BACKGROUND OF THE INVENTION

1. Field of the Invention

The invention relates to methods and compositions for controlling the central nervous system of humans or animals. More particularly, the invention relates to methods and compositions for temporarily alleviating the symptoms of hypersomnia or mental fatigue or drowsiness or suppressing appetite or for potentiating the effects of anti-depressant drugs.

2. Background of the Prior Art

Piperoxan or 2-piperidinomethyl-1,4-benzodioxan is a chemical compound having the following structural formula

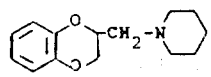

and is described in detail in U.S. Pat. No. 2,056,046. It has been used as an adrenergic blocking agent and in a diagnostic test for pheochromocytoma.

Mental fatigue or drowsiness are commonly observed in humans and animals. Drowsiness takes a form in hypersomnia, a term used generally to describe excessive sleeping. Further, persons suffering from depression have a tendency to sleep excessively. While various stimulants such as amphetamines have been used to treat some of the foregoing as well as suppress appetite, amphetamines have undesirable side-effects associated with their actions. Thus, it would be desirable to have available a compound which would act to temporarily overcome drowsiness or mental fatigue or hypersomnia or to suppress appetite without manifesting undesirable amphetamine-like side effects.

SUMMARY OF THE INVENTION

It has now been discovered that drowsiness or mental fatigue or hypersomnia may be temporarily overcome with the introduction of undesirable amphetamine-like side effects by the application of the methods disclosed and claimed herein.

The present invention relates to a method of temporarily alleviating symptoms of hypersomnia by administering to a person suffering from hypersomnia a composition comprising an effective amount of piperoxan or a pharmaceutically acceptable salt thereof together with a suitable pharmaceutical carrier.

The present invention also relates to a method of temporarily alleviating the symptoms of drowsiness or mental fatigue in humans by administering to a drowsy or mentally fatigued human a composition comprising an effective amount of piperoxan or a pharmaceutically acceptable salt thereof together with a suitable pharmaceutical carrier.

The present invention also relates to a method of potentiating the effects of anti-depressant drugs, that is, drugs for the treatment of mental depression, by administering to a depressed person about 20 to about 50% of a conventional effective dose of an anti-depressant drug in combination with, or concurrently with, a potentiating amount of piperoxan or a pharmaceutically acceptable salt thereof.

The present invention also relates to a composition comprising about 20 to about 50% of a conventional effective dose of an anti-depressant drug, a potentiating amount of piperoxan or a pharmaceutically acceptable salt thereof and a suitable pharmaceutical carrier.

The present invention also relates to a method for temporarily suppressing appetite in humans by administering to a human a composition comprising an effective amount of piperoxan or a pharmaceutically acceptable salt thereof together with a suitable pharmaceutical carrier.

DETAILED DESCRIPTION OF THE INVENTION

Piperoxan and its pharmaceutically acceptable salts may be made by the method described in U.S. Pat. No. 2,056,046, applicable portions of which are hereby incorporated by this reference. Pharmaceutically acceptable salts include conventional acid salts such as, for example, the alkali metal, alkaline earth metal, ammonium and organic amine salts of carboxylic acids and acid addition salts of the basic compounds formed with mineral acids, e.g. hydrochloric, sulfuric, nitric, phosphoric, etc. or with organic acids, e.g. acetic, maleic, etc.

The therapeutic amount of piperoxan which may be used in the present invention ranges from about 0.05 to about 50 mg/Kg and preferably from about 0.5 to about 25 mg/Kg.

Anti-depressant drugs which may be used in the present invention include monoamine oxidase inhibitors such as, for example, isocarboxazide, nialamide, phenelzine and tranylcypromine; and tricyclics such as, for example, imipramine, amitriptyline, desmethylimipramine (desipromine), desmethylamitriptyline and protriptyline.

While applicant does not necessarily rely on the following theory of action as to why piperoxan potentiates the effects of anti-depressant drugs, applicant subscribes to the theory that known anti-depressant drugs such as monoamine oxidase inhibitors or noradrenaline uptake inhibitors act by increasing noradrenaline receptor activity in the central nervous system. However, whenever the noradrenaline receptor activity is increased, compensatory mechanisms are initiated by the central nervous system to restore normal receptor activity. Applicant believes piperoxan acts by interfering with these compensatory mechanisms and thereby potentiates the effect of anti-depressant drugs by maintaining the higher noradrenaline receptor activity initially caused by the anti-depressant drug. In this manner, piperoxan can be used to potentiate the effects of anti-depressant drugs.

Further, piperoxan, when administered in combination with, or concurrently with, an anti-depressant drug, allows the use of lower doses, that is, 2-5 times less, anti-depressant drug to obtain the same effect as obtained with higher doses of an anti-depressant drug without piperoxan. This is a valuable result as most anti-depressant drugs have various side effects, such as cardiotoxicity and anti-cholinergic actions, which are reduced as the dose is decreased. For example, the recommended dose for the anti-depressant imipramine hydrochloride ("Tofranil") is about 25–50 mg orally 4 times a day. When given in combination with or concurrently with piperoxan as described, the dose range for the anti-depressant imipramine hydrochloride may be reduced 2–5 times, i.e. reduced from a range of about 100–200 mg daily to about 20–100 mg daily, thereby reducing the chances for undesirable side effects caused by high doses of drug, while maintaining the effectiveness of the drug.

The pharmaceutical composition containing piperoxan or containing piperoxan together with an antidepressant drug may be in a form suitable for oral use, for example, as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweeetening agents, flavoring agents, coloring agents and preserving agents in order to provide a pharmaceutically elegant and palatable preparation. Tablets contain the active ingredient in admixture with nontoxic pharmaceutically acceptable excipients which are suitable for manufacture of tablets. These excipients may be, for example, inert diluents, for example calcium carbonate, sodium carbonate, lactose, calcium phosphate or sodium phosphate; granulating and disintegrating agents, for example maize starch, or alginic acid; binding agents, for example starch, gelatine or acacia, and lubricating agents, for example magnesium stearate or stearic acid. The tablets may be uncoated or they may be coated by known techniques to delay disintegration and absorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate or kaolin, or as soft gelatine capsules wherein the active ingredient is mixed with an oil medium, for example arachis oil, liquid paraffin or olive oil.

Aqueous suspensions contain the active ingredients in admixture with excipients suitable for the manufacture of aqueous suspensions. Such excipients are suspending agents, for example sodium carboxymethyl cellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, for example polyoxyethylene sorbitol monooleate, or condensation product of ethylene oxide with partial esters derived from fatty acids and hexitol anhydrides, for example polyoxyethylene sorbitol monooleate. The said aqueous suspensions may also contain one or more preservatives, for example ethyl, or n-propyl, p-hydroxy benzoate, one or more coloring agents, one or more flavoring agents and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injection preparation, for example as a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol.

The pharmaceutical compositions containing piperoxan or containing piperoxan together with an antidepressant drug may be tabulated or otherwise formulated so that for every 100 parts by weight of the composition there are present between 5 and 95 parts by weight of the active ingredient or ingredients and preferably between 25 and 85 parts by weight of the active ingredient or ingredients. A preferred dosage rate for oral administration is of the order of 1–1,000 mg daily, optionally in divided doses.

From the foregoing formulation discussion, it is apparent that the compositions of this invention can be administered orally or parenterally. The term parenteral as used herein includes subcutaneous injection, intravenous, intramuscular, or intrasternal injection or infusion techniques.

This invention is further demonstrated by the following examples in which all parts are by weight.

EXAMPLE I

Male Sprague-Dawley rats (250 g) were operated upon in a stereotaxic instrument under halothane oxygen anesthesia two weeks before the starting of the EEG recordings. Four electrodes for cortical EEG recordings and two for EMG recordings were implanted by drilling small holes in the skull above the frontal and parietal cortex and inserting four female connecting pins and three screws. Two electrodes were placed in the neck muscle and connected to two female pins held in a position behind the cortical electrodes. The set-up was fixed to the skull with dental cement. The EEG records were distinguished into four different stages of activity: "waking," cortical low voltage fast activity and a high muscle tone; "slow wave sleep 1," low voltage fast activity interrupted by high amplitude slow waves and a moderate to high EMG activity; "slow wave sleep 2," continued high voltage slow waves and a marked decrease of muscle tone; "paradoxical sleep", a waking EEG with a complete disappearance of EMG activity except for some twitches. Each minute of the record was scored as belonging to one of these four stages.

The results are shown in Table 1. Piperoxan in a dose of 5 mg/kg produces a significant increase in waking by about 30 percent. The other stages of sleep are not significantly changed.

Table 1

The effect of piperoxan on sleep and waking in the rat

The EEG recording started at 9 a.m. immediately after the piperoxan (5 mg/kg, i.p.) or saline injection and lasted for 6 hr. Each animal was used for 4–5 days.

The first day saline was used, followed by drug on the second day. This schedule was then repeated. The values for sleep and waking are expressed as percent of total time. Six animals have been used. n = number of 6 hr. recordings.

| Treatment | n | Waking | Slow Wave Sleep 1 | Slow Wave Sleep 2 | Paradoxical Sleep |
|---|---|---|---|---|---|
| Saline | 12 | 19.5 ± 1.6 | 14.1 ± 1.7 | 50.5 ± 2.0 | 15.3 ± 0.7 |
| Piperoxan | 11 | 26.0 ± 1.6<sup>a</sup> | 11.6 ± 1.7 | 48.5 ± 2.5 | 13.6 ± 0.7 |

$^a p<0.01$ (Student's t-test)

EXAMPLE II

A mixture of 250 parts of piperoxan and 25 parts of lactose is granulated with suitable water and to this is added 100 parts of maize starch. The mass is passed through a 16-mesh screen. The granules are dried at a temperature below 60° C. The dry granules are passed through a 16-mesh screen and mixed with 3.8 parts of magnesium stearate. They are then compressed into tablets suitable for oral administration according to the method of this invention.

EXAMPLE III

A mixture of 50 parts of piperoxan, 3 parts of the calcium salt of lignin sulfonic acid, and 237 parts of water is ball-milled until the size of substantially all the particles of piperoxan is less than 10 microns. The suspension is diluted with a solution containing 3 parts of sodium carboxymethylcellulose and 0.9 part of the butyl ester of p-hydroxybenzoic acid in 300 parts of water. There is thus obtained an aqueous suspension suitable for oral administration for therapeutic purposes.

EXAMPLE IV

A mixture of 250 parts of piperoxan, 50 parts imipramine hydrochloride, 200 parts of maize starch and 30 parts of alginic acid is mixed with a sufficient quantity of a 10% aqueous paste of maize starch and granulated. The granules are dried in a current of warm air and the dry granules are then passed through a 16-mesh screen, mixed with 6 parts of magnesium stearate and compressed into tablet form to obtain tablets suitable for oral administration.

EXAMPLE V

A mixture of 500 parts of piperoxan, 60 parts of maize starch and 20 parts of gum acacia is granulated with a sufficient quantity of water. The mass is passed through a 12-mesh screen and the granules are dried in a current of warm air. The dry granules are passed through a 16-mesh screen, mixed with 5 parts of magnesium stearate and compressed into tablet form suitable for oral administration.

I claim:

1. A method for temporarily alleviating symptoms of depression in humans by administering to a human suffering from depression a composition comprising an effective amount of a compound selected from the group consisting of piperoxan and a pharmaceutically acceptable salt thereof together with a suitable pharmaceutical carrier.

* * * * *